United States Patent [19]

Maeda et al.

[11] Patent Number: 4,860,574
[45] Date of Patent: Aug. 29, 1989

[54] PARAMAGNETIC OXYGEN ANALYZER

[75] Inventors: Masato Maeda; Hideo Takeuchi, both of Tokyo, Japan

[73] Assignee: Yokogawa Electric Corporation, Tokyo, Japan

[21] Appl. No.: 209,431

[22] Filed: Jun. 21, 1988

[30] Foreign Application Priority Data

Jun. 29, 1987 [JP] Japan .................................. 62-161601
Dec. 24, 1987 [JP] Japan .................................. 62-327916

[51] Int. Cl.$^4$ .......................................... G01N 27/76
[52] U.S. Cl. ................................... 73/27 A; 324/204
[58] Field of Search ................... 73/27 A, 25; 324/204

[56] References Cited

U.S. PATENT DOCUMENTS

| 3,045,474 | 1/1962 | Ebbinghaus | 73/27 A |
| 3,302,448 | 2/1967 | Mocker | 73/27 A |
| 3,471,776 | 10/1969 | Eller et al. | 73/27 A |
| 3,486,364 | 12/1969 | Luft | 73/27 A |

FOREIGN PATENT DOCUMENTS

| 2531849 | 1/1977 | Fed. Rep. of Germany | 73/27 A |
| 2701084 | 7/1978 | Fed. Rep. of Germany | 73/27 A |
| 131095 | 11/1978 | Japan | 324/204 |
| 139798 | 10/1979 | Japan | 324/204 |

Primary Examiner—Hezron E. Williams
Attorney, Agent, or Firm—Moonray Kojima

[57] ABSTRACT

A closed loop-like measuring passage is provided with two openings at symmetrical positions, and a sample gas is introduced through on opening into the passage and discharged therefrom through the other opening. A bypass pipe is connected to the measuring passage midway therealong, and a stable purge gas of known composition is introduced into the pipe from the center thereof. A magnetic field is generated in one of the two connecting portions between the bypass pipe and the measuring passage, and the oxygen gas attracting action of the field results in a change in the ratio of the split of the purge gas stream introduced into the bypass pipe and split into two streams. This change is detected by a pair of purge gas stream detecting sensors provided inside the bypass pipe symmetrically with respect to the portion through which the purge gas is introduced, and the thus detected signals are processed to obtain the difference between them which gives the oxygen gas concentration in the sample gas.

3 Claims, 6 Drawing Sheets

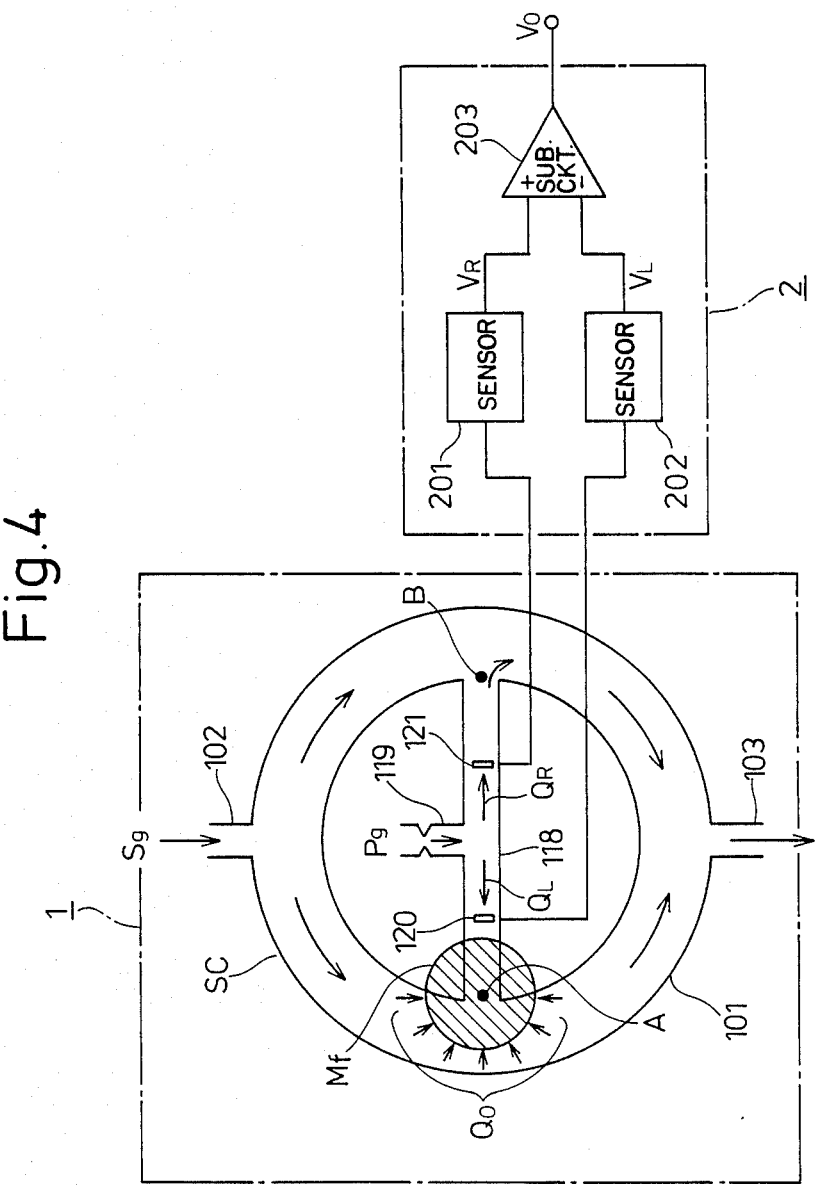

4,860,574

PARAMAGNETIC OXYGEN ANALYZER

BACKGROUND OF THE INVENTION

1. Field of the Invention

This invention relates to a paramagnetic oxygen analyzer for detecting the concentration of oxygen gas contained in a sample gas, through utilization of the magnetic properties of the oxygen gas.

2. Discussion of the Prior Art

Paramagnetic oxygen analyzers are classified as a gas analyzer which measures an oxygen concentration in a sample gas by utilizing the property of oxygen gas that has a very large susceptibility as compared to the other gases in the sample gas. Depending on the principle of measurement used, there are three known types, (1) the thermomagnetic type, (2) the magnetic susceptibility type, and (3) the magnetic pressure type.

The thermomagnetic type is shown in FIG. 1 and comprises a measuring cell 1, a closed loop-like measuring passage 101 forming a measuring chamber, an inlet 102 and an outlet 103 for a sample gas Sg disposed at symmetrical positions along the measuring passage 101, and a bypass pipe 104 connected to two circular measuring passage segments which extend between inlet 102 and outlet 103. A heating resistance wire $R_1$ is wound around bypass pipe 104, and a magnetic field Mf is generated in one of the connecting portions between bypass pipe 104 and measuring passage 101. With resistors $R_1$, $R_2$ and $R_3$ forming a bridge, a detecting circuit is adapted to measure an unbalanced voltage appearing between the midpoint of $R_1$ and the connecting point of $R_2$ and $R_3$.

The operation of the foregoing analyzer is as follows. Where oxygen gas is included in the sample gas, oxygen molecules are attracted to magnetic field Mf to flow into bypass pipe 104. The oxygen molecules having flowed in, are heated by heating resistance wire $R_1$. When heated, the susceptibility of the oxygen molecules decreases, so that the force with which the oxygen molecules are attracted to magnetic field Mf weakens. Then, the oxygen molecules are pushed by new low-temperature oxygen molecules coming in, so that they flow through bypass pipe 104. The bridge circuit detects a temperature change due to such a magnetic wind. Thus, the oxygen concentration in the sample gas Sg can be measured.

However, in this type of analyzer, the sample gas introduced into bypass pipe 104 by the attractive action of the magnetic field Mf is heated, so that the heat conductivity, heat capacity, viscosity, etc, of the gas components, other than the oxygen gas included in the sample gas Sg, cause an adverse influence which result in an interference error.

The magnetic susceptibility type is shown in FIG. 2 and comprises diamagnetic dumbbells 105 and 106 suspended horizontally in a magnetic field Mf generated by pole pieces 107,108,109,110, and a sample gas Sg is caused to flow through such an area. Servomex markets a typical oxygen analyzer of this type. Oxygen molecules, included in the sample gas Sg, are attracted to the magnetic field Mf, so that diamagnetic dumbbells 105 and 106 are pushed out of magnetic field Mf. The positional displacement, which may be the torsion, of dumbbells 105 and 106 corresponds to the oxygen concentration. Thus, by detecting the positional displacement and supplying a feedback current, corresponding to the displacement, to a coil 111 wound around dumbbells 105,106, such that a counter torque produced by means of an electromagnetic effect returns dumbbells 105,106 to their initial state, it is possible to obtain the oxygen concentration from the feedback current.

However, disadvantageously, in this type of analyzer, because the pair of dumbbells is suspended horizontally in the magnetic field, its structure is complicated and susceptible to mechanical shock and vibration.

The magnetic pressure type is shown in FIG. 3. An example of such analyzer is disclosed in German Pat. No. 2701084. In FIG. 3, similar members as shown in FIG. 1 are designated by the same reference symbols and will not be described hereat for clarity of description. In addition, the analyzer comprises a connecting pipe 112 for connecting two measuring passage segments which extend between inlet 102 and outlet 103, a micro-differential pressure detector 113, such as a capacitor microphone, provided at the center of the pipe, and a purge gas passage 114 which allows a purge gas Pg, supplied from an inlet 115, to flow through throttles 116 and 117, into pipe segments 112 located on either side of detector 113. Magnetic fields Mf, Mf' are generated alternately and are in the two connecting portions between pipe 112 and measuring chamber 101.

In the FIG. 3 embodiment, oxygen molecules included in sample gas Sg are attracted to each magnetic field Mf,Mf', so that the background pressure of an area, where the magnetic field is generated, increases. Because magnetic fields Mf and Mf' are generated alternately, an alternating signal whose amplitude corresponds to the oxygen concentration, is produced by detector 113.

In this type of analyzer, although there is only a small amount of interference error, detection is susceptible to mechanical vibration and shock being applied to the detection portion because only one detector is used. Furthermore, because the detector 113 is configured so as to detect a micro pressure transmitted to the detecting portion, it is susceptible to background pressure change. Thus, the device has the disadvantage that a measurement error will occur when a pressure change on the downstream side of outlet 103 is fed back.

Thus, there is still a need in the art for a paramagnetic oxygen analyzer that is substantially error free.

SUMMARY OF THE INVENTION

Accordingly, an object of the invention is to overcome the above and other deficiencies and disadvantages of the prior art.

Another object is to provide a paramagnetic oxygen analyzer which is substantially free of interference error due to gas components, other than oxygen gas, included in a sample gas.

A further object is to provide such an analyzer which is simple in structure and least susceptible to mechanical shock and vibration.

A still further object is to provide a paramagnetic oxygen analyzer which is not influenced by background pressure changes on the downstream side of a sensor, and provides a detection output having a large signal component.

The foregoing and other objects and advantages are attained by the invention which encompasses a paramagnetic oxygen analyzer comprising a measuring chamber having a closed loop-like measuring passage with an inlet and an outlet for a sample gas provided at symmetrical positions, and including a bypass pipe with a purge gas inflow port, provided at the center thereof, which is connected to the passage at intermediate positions between the inlet and the outlet; means for creating a magnetic field, provided in one of the connecting portions between the bypass pipe and the closed loop-like measuring passage; and a pair of purge gas stream detecting sensors, provided inside the bypass pipe at symmetrical positions so that the purge gas inflow port is located between the sensors; wherein the concentration of oxygen gas in the sample gas is measured by detecting the changes of purge gas streams passing through the respective sensing portions of the sensors by means of the sensors, and obtaining a signal difference between the thus detected changes.

In operation, when the oxygen gas in the sample gas is attracted to the magnetic field, this results in a change in the ratio of split of the purge gas, which purge gas is introduced through the purge gas inflow port and split into two streams that flow through the bypass pipe. This change is detected by the pair of purge gas detector sensors, which are made, for example, of temperature sensing resistance elements. Because these latter sensors are disposed inside the bypass pipe through which the purge gas is flowing, each detection output has a large signal component. After subjecting the detection signals to zero correction, non-linear correction, etc, a detecting circuit obtains the difference between the two signals corrected to provide a signal corresponding to the oxygen gas concentration in the sample gas.

BRIEF DESCRIPTION DRAWINGS

FIG. 4 is a schematic diagram depicting an illustrative embodiment of the invention.

Figure 7A:
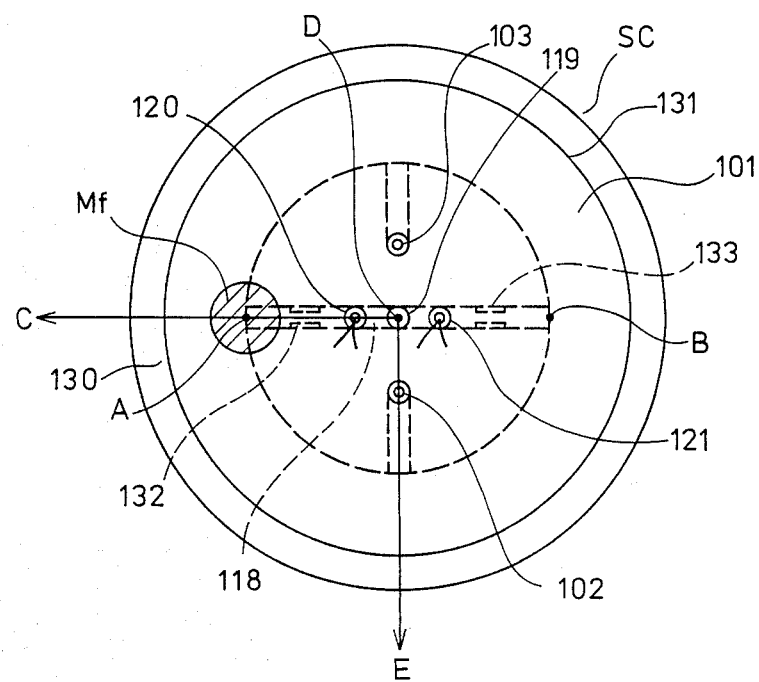
Figure 7B:
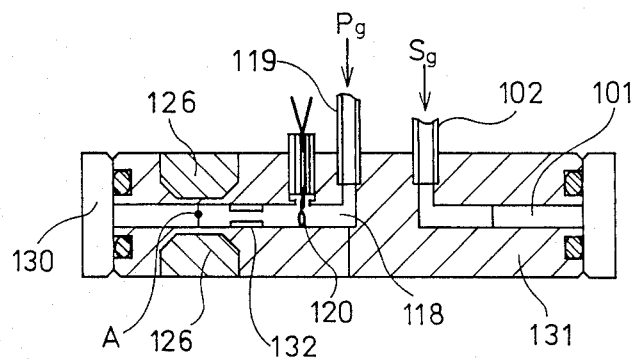

FIGS. 7(A), 7(B) are diagrams depicting a measuring cell usable in the invention, wherein FIG. 7(A) is a plan view, and FIG. 7(B) is a sectional view.

Figure 8:
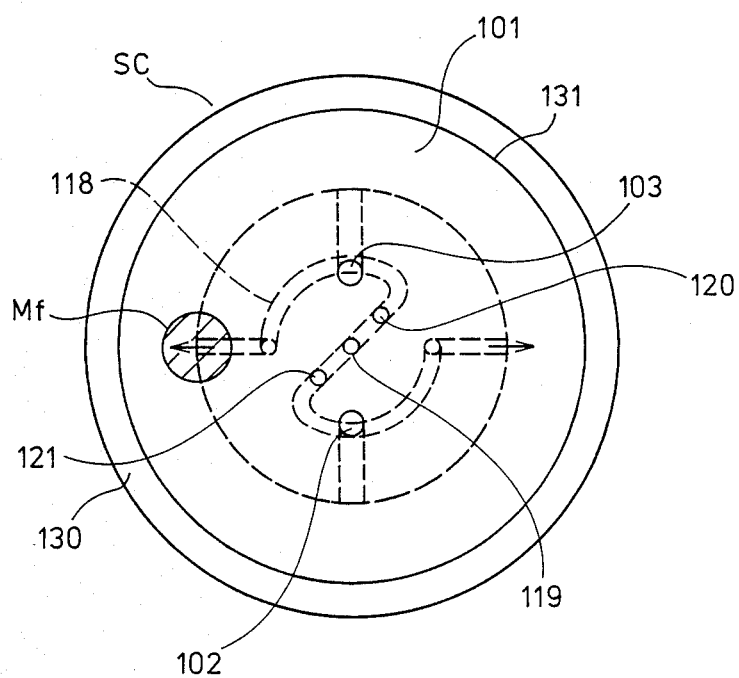

FIG. 8 a plan view depicting another measuring cell usable in the invention.

DETAILED DESCRIPTION OF PREFERRED EMBODIMENTS.

Figure 1:
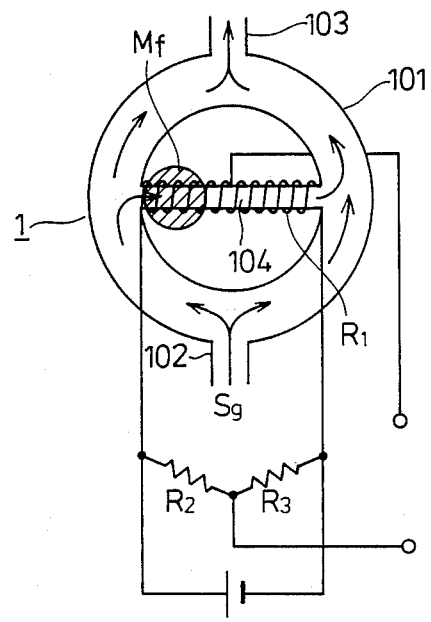
FIG. 1 depicts a known thermomagnetic type oxygen analyzer.
Figure 2:
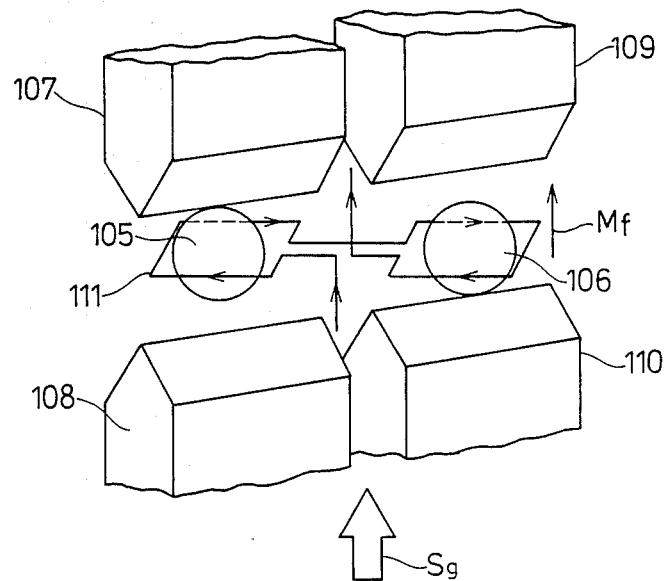
FIG. 2 depicts a known magnetic susceptibility type oxygen analyzer.
Figure 3:
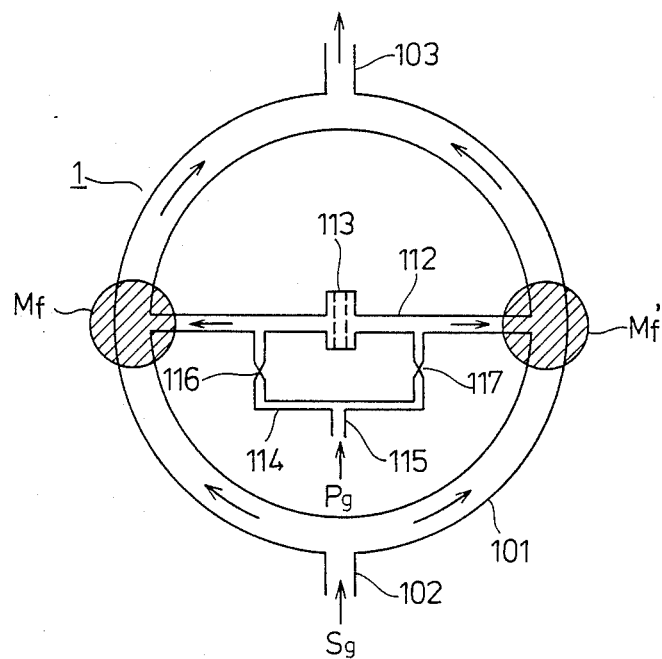
FIG. 3 depicts a known magnetic pressure type oxygen analyzer.

In FIG. 4, surrounded by a dotted chain line, are a detecting section 1 and a converting section 2. Detecting section 1 comprises a measuring cell SC and other members which are substantially identical with those shown in FIGS. 1 and 3 and are designated by the same reference symbols and will not be described hereat to avoid duplication. The measuring cell SC comprises a bypass pipe 118 disposed at an intermediate position between inlet 102 and outlet 103 for connecting two circular measuring passage segments, and an inflow port 119 for a purge gas Pg disposed at the center of bypass pipe 118. Out of connecting portions A and B between bypass pipe 118 and measuring passage 101, one connecting portion A is provided with means for generating a magnetic field Mf, which is made, for example, of a permanent magnet.

Resistance sensors 120 and 121 are for purposes of detecting the purge gas stream, and sensing the temperature, and are disposed in bypass pipe 118 at symmetrical positions so that purge gas inflow port 119 is disposed between the sensors 120,121. Sensors 120,121 are made, for example, of thermistors having a large resistance temperature coefficient.

Converting section 2 comprises temperature control circuits 201 and 202 connected to corresponding sensors 120 and 121, and a subtracting circuit 203 which is supplied with output signals from circuits 201 and 22.

In the FIG. 4 embodiment, where no oxygen gas is included in the sample gas Sg, there is no attraction of the oxygen gas to magnetic field Mf, so that no changes appear in the flow velocities of the split purge gas streams $Q_L$ and $Q_R$ which advance toward the connecting portions A and B inside the bypass pipe 118. On the other hand, where there is oxygen gas included in the sample gas Sg, the oxygen gas is attracted to the magnetic field Mf, so that oxygen gas streams occur, as indicated by arrows Qo. As a result, the flow velocity of $Q_L$ decreases, whereas the flow velocity of $Q_R$ increases.

The changes in each of the purge gas streams $Q_L$ and $Q_R$, separately advancing inside bypass pipe 118, corresponds to the oxygen concentration in sample gas Sg, and is detected by each temperature sensing resistance sensors 120,121 through the change of resistance thereof. In connection with the resistance of each sensor changing in response to the flow velocity of each purge gas stream $Q_L$, $Q_R$, feedback is provided from each temperature control circuit 201, 202 to change the source voltage of each sensor 120, 121 so that the temperature of each sensor, i.e. its resistance, is controlled and maintained constant. The magnitude of each of such feedback signals corresponds to the flow velocity of each purge gas stream $Q_L$, $Q_R$. Thus, output signals $V_R$ and $V_L$ of temperature control circuits 201 and 202 are supplied to subtracting circuit 203 where the difference between these signals is obtained, so that an output voltage Vo is produced.

In the analyzer of FIG. 4, the sensors 120 and 121 are disposed inside the pipe line through which the purge gas streams $Q_L$ and $Q_R$ are always flowing. Advantageously, the analyzer is least susceptible to shock and vibration from the outside because each of the detection outputs is obtained with a large signal component and they are processed in the subtracting circuit 203 to obtain the difference therebetween.

Figure 5:
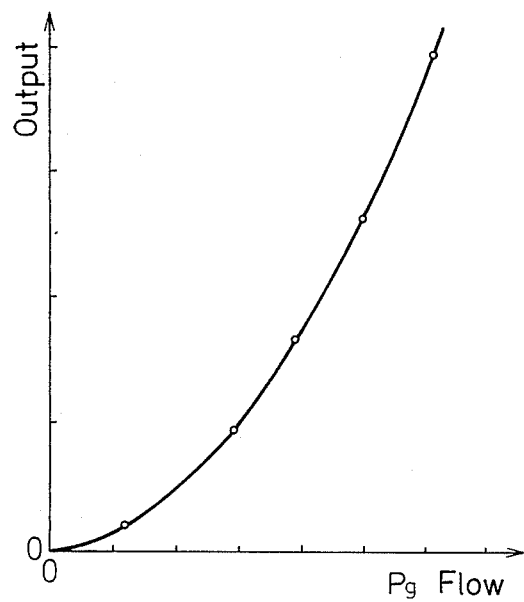
FIG. 5 is a graph depicting the detection characteristics of a sensor versus the flow rate of a purge gas.

However, because a non-linear relationship exists between the detection output of each sensor 120 and 121 and the flow rate, ie. velocity, of each purge gas stream $Q_L$, $Q_R$, as shown in FIG. 5, if the flow rate of each purge gas stream $Q_L$, $Q_R$ changes, the difference between the detection outputs of sensors 120 and 121, which is obtained through simple subtraction, involves a measurement error. The embodiment of FIG. 6 can avoid such measurement error.

Figure 6:
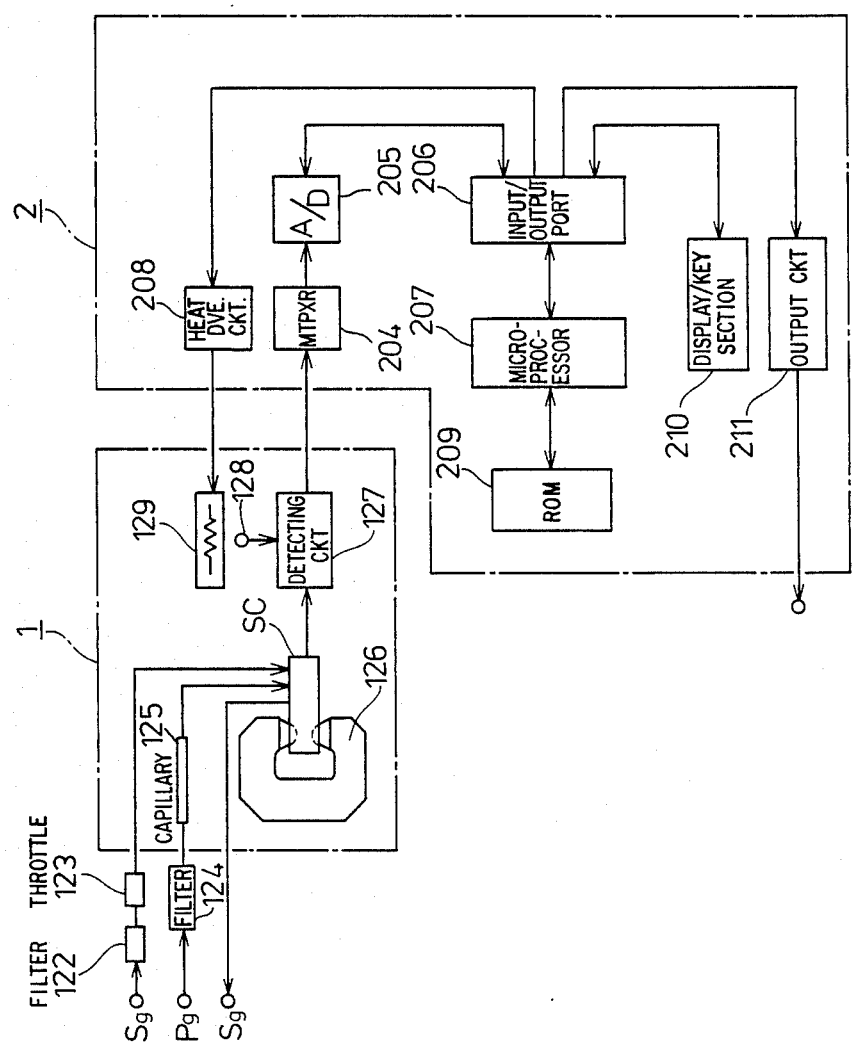
FIG. 6 is a schematic diagram depicting another illustrative embodiment of the invention.

In FIG. 6, members which are substantially identical to those shown in FIG. 4 bear the same reference symbols and will not be further discussed hereat for sake of clarity of discussion. The detecting section 1 is held in a constant temperature bath, and sample gas Sg is supplied through a filter 122 and a throttle 123 to measuring cell SC. Purge gas Pg is supplied through a filter 124 and a capillary 125, to measuring cell SC. The detecting section 1 further comprises a magnet or pole piece 126, a detecting circuit 127, a temperature detecting element 128, and a heater 129. Magnet 126 generates a magnetic field.

The block of measuring cell SC will now be describe reference to FIGS. 7(A) and 7(B), wherein FIG. 7(B) is a sectional view taken along lines C-D-E in FIG. 7(A). Measuring cell SC comprises an outer ring 130 and an inner disc 131. The ring-like measuring passage, forming a closed loop, is formed by sealing a groove provided in the periphery of disc 131 with ring 130. Inlet 102 and outlet 103, which are used for sample gas Sg, are disposed in a central portion, inside ring-like measuring passage 101, on the upper side of disc 131. Pole pieces 126 are embedded in disc 131. Throttles 132 and 133 are disposed in bypass pipe 118 at symmetrical positions so that the purge gas inflow port 119 is placed between the throttles.

Referring again to FIG. 6, in the converting section 2, is provided a multiplexer 204. The output of detecting circuit 127, selected by the multiplexer, is converted by an A/D converting circuit 205 into a digital quantity and applied through an input/output port 206 to a microprocessor 207. On the other hand, a signal detected by temperature detecting element 128 is also applied through detecting circuit 127, A/D converting circuit 205, and input/output port 206 to microprocessor 207, and a temperature control signal is applied to a heater driving circuit 208, so that heater 129 is driven and temperature controlled. A ROM 209 is provided with a processing program and the like stored therein. A display/key section 210 and an output circuit 211 are provided as shown.

The operation of the FIG. 6 embodiment is as follows. Before start of measurement, sensors 120 and 121 are actuated to perform detection with no purge gas Pg being supplied. The thus obtained detection output signals are stored in microprocessor 207, as zero error signals. Then, measurement is made while passing purge gas Pg, and the zero error signals are subtracted from the obtained detection signals to perform zero correction.

There is a non-linear relationship between the flow rate of purge gas Pg and the detection output of each sensor 120,121, as shown in the graph of FIG. 5. This relationship is that previously found. If the detection output has a square-law characteristic in relation to the purge gas flow rate, as shown in FIG. 5, the following computation is performed to subject the outputs of sensors 120 and 121 to zero correction and non-linear correction so that oxygen gas concentration output Vo is obtained as follows.

$$V_o = K\{(V_R - V_{Ro})^{\frac{1}{2}} - (V_L - V_{LO})^{\frac{1}{2}}\} \tag{1}$$

wherein $V_L$ is the detection output signal from sensor 120 on the magnetic field side, $V_R$ is the detection output signal from sensor 121 on the no magnetic field side, $V_{Lo}$ is the detection output signal from sensor 120 on the magnetic field side with zero purge gas flow rate, $V_{Ro}$ is the detection output signal from sensor 121 on the no magnetic field side with zero purge gas flow rate, and K is a constant.

Where sample gas Sg includes such gases as $H_2$ or He, having a large diffusion coefficient, such a gas diffuses through connecting portions A and B into bypass pipe 118 in opposition to the flowing of purge gas Pg. The diffusion gas has an exponential concentration distribution spreading from the connecting portions A and B toward sensors 120 and 121, and gives a concentration $C_N(x)$ expressed by the following equation at the position of sensors 120 and 121, so that a thermal influence is imposed on the sensors to result in an output error:

$$C_N(x) = C_{No} \cdot \exp\{-(v \cdot x)/Dn\} \tag{2}$$

wherein CNo is the concentration of the diffusion gas at the connecting portion A or B, v is the flow velocity of purge gas Pg, x is the distance from the connecting portion A,B to sensor 120,121, and Dn is the diffusion coefficient of the diffusion gas.

As will be appreciated from the equation (2), the proportion of diffusion decreases exponentially as the flow velocity v of purge gas Pg is increased or the distance x from connection portion A,B to sensor 120,121 is increased. In the embodiment of FIG. 7, the throttles 132 and 133 of a pair, are provided so as to put the purge gas inflow port 119 therebetween. Thus, the flow velocity of purge gas Pg is increased by means of these throttles to lessen the influence of the diffusion gas. For reference, provisions for increasing the flow velocity of the purge gas can be implemented by increasing the flow rate of the purge gas. However, this possibility cannot be adopted because purge gas is quickly consumed. In the embodiment of FIG. 8, bypass pipe 118 is made into the form of an inverted S-shape so that the distance from connecting portion A,B to sensor 120,121 is long. Thus, the influence of the diffusion gas is lessened.

According to the invention, (1) the sensors are disposed inside the bypass pipe through which the purge gas is flowing and thus are not in direct contact with the sample gas. Thus, the analyzer hardly receives an interference error due to gas components other hand the oxygen gas included in the sample gas. (2) The sensors detect, the purge gas streams flowing inside the bypass pipe to provide the detection output signals with large signal components, so that the analyzer is hardly influenced by background pressure variations on the downstream side of each sensor. (3) The analyzer is simple in structure and is configured so as to obtain the difference between the detection output signals from the two sensors so that mechanical shock and vibration being applied to the sensors are cancelled out and no influence exerted by these factors appear in the output. (4) In the case of the embodiment of FIG. 6, zero error and non-linear error included in the detection output signals from the sensors are compensated, so that they do not influence the measurement results. (5) where the measuring cell shown in FIGS. 7(A),7(B) or FIG. 8 is used, the influence of the diffusion gas included in the sample gas can be eliminated.

FIG. 8 depicts a measuring cell SC, which is similar to the measuring cell depicted in FIG. 7(A), except for the configuration of the bypass pipe 118 (it being S shaped in FIG. 8) and the location of the sensors 120,121 and inflow port 119 and inlet and outlet 102, and 103 being exposed to the bypass pipe 118 as depicted.

The foregoing is descriptive of the principles of the invention. Numerous other modifications and extensions thereof would be apparent to the worker skilled in the art. All such modifications and extensions are to be considered to be within the spirit and scope of the invention.

What is claimed is:
1. A paramagnetic oxygen analyzer comprising a measuring chamber comprising a closed loop-like measuring passage, said passage having an inlet and an outlet disposed at symmetrically opposing positions for inletting and outletting a sample gas through said loop-like measuring passage, and a bypass pipe disposed between two parts of said loop-like measuring passage and generally at an intermediate position between said inlet and outlet, said bypass pipe having an inflow port disposed generally at the center thereof for inletting of a purge gas to said bypass pipe, whereby two connecting portions are formed between the bypass pipe and the loop-like measuring passage;

means for generating a magnetic field, said means being disposed in one of said two connecting portions; and a pair of purge gas stream detecting sensors disposed inside of said bypass pipe at symmetrical positions on either side of said inflow port;

wherein the concentration of an oxygen gas contained in the sample gas is measured by said detecting sensors detecting changes of purge gas streams passing through said respective sensors and by producing a signal difference between the thus detected changes.

2. The analyzer of claim 1, wherein said pair of sensors comprise a pair of resistance sensors for detecting purge gas stream, and sensing temperature, said resistance sensors being disposed inside the bypass pipe at symmetrical positions so that the purge gas inflow port is located between the sensors, wherein two detection signals obtained by the resistance sensors are subjected to zero error correction, the resulting two signals zero-error-corrected are subjected to non-linear correction which is necessitated by the sensors, and the then resulting two signals are processed to obtain the difference therebetween which is provided as a measurement output.

3. The analyzer of claim 4, wherein further comprising a pair of throttles disposed inside the bypass pipe at symmetrical positions so that the purge gas inflow port is located between the throttles so that the flow velocities of the purge gas streams are increased by means of the throttles to eliminate the influence of any diffusion gases included in the sample gas.

* * * * *